(12) United States Patent
Couture et al.

(10) Patent No.: US 10,124,124 B2
(45) Date of Patent: Nov. 13, 2018

(54) COMPUTER ASSISTED SUBCHONDRAL INJECTION

(71) Applicant: ORTHOSOFT, INC., Montreal (CA)

(72) Inventors: Pierre Couture, Montreal (CA); Louis-Philippe Amiot, Hampstead (CA); Laurence Mercier, Montreal (CA)

(73) Assignee: ZIMMER, INC., Warsaw, IN (US)

( * ) Notice: Subject to any disclaimer, the term of this patent is extended or adjusted under 35 U.S.C. 154(b) by 455 days.

(21) Appl. No.: 14/301,873

(22) Filed: Jun. 11, 2014

(65) Prior Publication Data
US 2014/0364807 A1 Dec. 11, 2014

Related U.S. Application Data

(60) Provisional application No. 61/833,652, filed on Jun. 11, 2013.

(51) Int. Cl.
*A61M 5/42* (2006.01)
*A61B 17/34* (2006.01)
*A61B 17/17* (2006.01)
*G16H 50/50* (2018.01)
*G06F 19/00* (2018.01)
*A61B 34/20* (2016.01)
*A61B 34/10* (2016.01)

(52) U.S. Cl.
CPC .......... *A61M 5/427* (2013.01); *A61B 17/1764* (2013.01); *A61B 17/3472* (2013.01); *G06F 19/00* (2013.01); *G16H 50/50* (2018.01); *A61B 2034/105* (2016.02); *A61B 2034/2055* (2016.02); *A61B 2034/2068* (2016.02)

(58) Field of Classification Search
CPC .......... A61B 17/3472; A61B 17/1764; A61M 5/427; A61M 25/06; G06F 19/3437
USPC ................................. 600/417, 424, 426, 429
See application file for complete search history.

(56) References Cited

U.S. PATENT DOCUMENTS 4,841,975 A 6/1989 Woolson
5,098,383 A 3/1992 Hemmy et al.
(Continued)

FOREIGN PATENT DOCUMENTS

AU 2004293091 A1 6/2005
AU 2004293104 A1 6/2005
(Continued)

OTHER PUBLICATIONS

Taylor et al, "Computer-Integrated Surgery, Technology and Clinical Applications", The MIT Press, Cambridge, MA, London, UK, pp. 451-463.
(Continued)

*Primary Examiner* — Matthew Lawson
(74) *Attorney, Agent, or Firm* — Norton Rose Fulbright Canada LLP

(57) ABSTRACT

A method for assisting subchondral injection comprising creating a model of bone and soft tissue of a patient. At least one void is modeled in the bone from the model of bone and soft tissue. An injection site is identified from the model of bone and soft tissue and modeling of the at least one void. Data is output for guiding at least in the locating of the injection site and drilling of the bone to reach the void. A patient-specific jig for subchondral injection may be created based on the injection site location.

16 Claims, 4 Drawing Sheets

(56) References Cited

U.S. PATENT DOCUMENTS

| | | | |
|---|---|---|---|
| 5,490,854 | A | 2/1996 | Fisher et al. |
| 5,768,134 | A | 6/1998 | Swaelens et al. |
| 5,871,018 | A | 2/1999 | Delp et al. |
| 5,916,219 | A | 6/1999 | Matsuno et al. |
| 7,357,057 | B2 | 4/2008 | Chiang |
| 7,468,075 | B2 | 12/2008 | Lang et al. |
| 7,510,557 | B1 | 3/2009 | Bonutti |
| 7,534,263 | B2 | 5/2009 | Burdulis |
| 7,618,451 | B2 | 11/2009 | Berez et al. |
| 7,634,119 | B2 | 12/2009 | Tsougarakis et al. |
| 7,717,956 | B2 | 5/2010 | Lang |
| 7,796,791 | B2 | 9/2010 | Tsougarakis et al. |
| 7,799,077 | B2 | 9/2010 | Lang et al. |
| 7,806,896 | B1 | 10/2010 | Bonutti |
| 7,806,897 | B1 | 10/2010 | Bonutti |
| 7,967,868 | B2 | 6/2011 | White et al. |
| 7,981,158 | B2 | 7/2011 | Fitz et al. |
| 8,002,748 | B2 | 8/2011 | Donovan |
| 8,062,302 | B2 | 11/2011 | Lang et al. |
| 8,066,708 | B2 | 11/2011 | Lang et al. |
| 8,070,752 | B2 | 12/2011 | Metzger et al. |
| 8,077,950 | B2 | 12/2011 | Tsougarakis et al. |
| 8,083,745 | B2 | 12/2011 | Lang et al. |
| 8,092,465 | B2 | 1/2012 | Metzger et al. |
| 8,094,900 | B2 | 1/2012 | Steines et al. |
| 8,105,330 | B2 | 1/2012 | Fitz et al. |
| 8,122,582 | B2 | 2/2012 | Burdulis, Jr. et al. |
| 8,133,234 | B2 | 3/2012 | Meridew et al. |
| 8,160,345 | B2 | 4/2012 | Pavlovskaia et al. |
| 8,175,683 | B2 | 5/2012 | Roose |
| 8,221,430 | B2 | 7/2012 | Park et al. |
| 8,234,097 | B2 | 7/2012 | Steines et al. |
| 8,241,293 | B2 | 8/2012 | Stone et al. |
| 8,282,646 | B2 | 10/2012 | Schoenefeld et al. |
| 8,298,237 | B2 | 10/2012 | Schoenefeld |
| 8,337,501 | B2 | 12/2012 | Fitz et al. |
| 8,337,507 | B2 | 12/2012 | Lang et al. |
| 8,343,218 | B2 | 1/2013 | Lang et al. |
| 8,366,771 | B2 | 2/2013 | Burdulis et al. |
| 8,377,129 | B2 | 2/2013 | Fitz et al. |
| 8,415,407 | B2 * | 4/2013 | Beyar .............. A61B 17/1671 523/117 |
| 8,439,926 | B2 | 5/2013 | Bojarski et al. |
| 8,460,304 | B2 | 6/2013 | Fitz et al. |
| 8,480,754 | B2 | 7/2013 | Bojarski et al. |
| 8,500,740 | B2 | 8/2013 | Bojarski et al. |
| 8,529,568 | B2 | 9/2013 | Bouadi |
| 8,529,630 | B2 | 9/2013 | Bojarski |
| 8,585,708 | B2 | 9/2013 | Fitz et al. |
| 8,545,569 | B2 | 10/2013 | Fitz et al. |
| 8,551,099 | B2 | 10/2013 | Lang |
| 8,551,102 | B2 | 10/2013 | Fitz et al. |
| 8,551,103 | B2 | 10/2013 | Fitz et al. |
| 8,551,169 | B2 | 10/2013 | Fitz et al. |
| 8,556,906 | B2 | 10/2013 | Fitz et al. |
| 8,556,907 | B2 | 10/2013 | Fitz et al. |
| 8,556,971 | B2 | 10/2013 | Lang |
| 8,556,983 | B2 | 10/2013 | Bojarski et al. |
| 8,561,278 | B2 | 10/2013 | Fitz et al. |
| 8,562,611 | B2 | 10/2013 | Fitz et al. |
| 8,562,618 | B2 | 10/2013 | Fitz et al. |
| 8,568,479 | B2 | 10/2013 | Fitz et al. |
| 8,568,480 | B2 | 10/2013 | Fitz et al. |
| 8,617,172 | B2 | 12/2013 | Fitz et al. |
| 8,617,242 | B2 | 12/2013 | Philipp |
| 8,623,026 | B2 | 1/2014 | Wong et al. |
| 8,634,617 | B2 | 1/2014 | Tsougarakis et al. |
| 8,638,998 | B2 | 1/2014 | Steines et al. |
| 8,641,716 | B2 | 2/2014 | Fitz et al. |
| 8,644,973 | B2 * | 2/2014 | Bake ................ A61F 2/30756 606/88 |
| 8,657,827 | B2 | 2/2014 | Fitz et al. |
| 8,682,052 | B2 | 3/2014 | Fitz et al. |
| 2002/0055679 | A1 * | 5/2002 | Sati ................ A61B 17/1714 600/424 |
| 2003/0055502 | A1 | 3/2003 | Lang et al. |
| 2003/0216669 | A1 | 11/2003 | Lang et al. |
| 2004/0133276 | A1 | 7/2004 | Lang et al. |
| 2004/0138754 | A1 | 7/2004 | Lang et al. |
| 2004/0147927 | A1 | 7/2004 | Tsougarakis et al. |
| 2004/0153079 | A1 | 8/2004 | Tsougarakis et al. |
| 2004/0204644 | A1 | 10/2004 | Tsougarakis et al. |
| 2004/0204760 | A1 | 10/2004 | Fitz et al. |
| 2004/0236424 | A1 | 11/2004 | Berez et al. |
| 2005/0234461 | A1 | 10/2005 | Burdulis et al. |
| 2005/0267584 | A1 | 12/2005 | Burdulis et al. |
| 2006/0111722 | A1 | 5/2006 | Bouadi |
| 2007/0083266 | A1 | 4/2007 | Lang |
| 2007/0100462 | A1 | 5/2007 | Lang et al. |
| 2007/0156171 | A1 | 7/2007 | Lang et al. |
| 2007/0157783 | A1 | 7/2007 | Chiang |
| 2007/0198022 | A1 | 8/2007 | Lang et al. |
| 2007/0226986 | A1 | 10/2007 | Park et al. |
| 2007/0233141 | A1 | 10/2007 | Park et al. |
| 2007/0233269 | A1 | 10/2007 | Steines et al. |
| 2007/0250169 | A1 | 10/2007 | Lang |
| 2008/0114370 | A1 | 5/2008 | Schoenefeld |
| 2008/0147072 | A1 | 6/2008 | Park et al. |
| 2008/0161815 | A1 | 7/2008 | Schoenefeld et al. |
| 2008/0171930 | A1 | 7/2008 | Abolfathi et al. |
| 2008/0195216 | A1 | 8/2008 | Philipp |
| 2008/0243127 | A1 | 10/2008 | Lang et al. |
| 2008/0275452 | A1 | 11/2008 | Lang et al. |
| 2008/0281328 | A1 | 11/2008 | Lang et al. |
| 2008/0281329 | A1 | 11/2008 | Fitz et al. |
| 2008/0281426 | A1 | 11/2008 | Fitz et al. |
| 2008/0287954 | A1 | 11/2008 | Kunz et al. |
| 2009/0024131 | A1 | 1/2009 | Metzgu et al. |
| 2009/0088753 | A1 | 4/2009 | Aram et al. |
| 2009/0088754 | A1 | 4/2009 | Aker et al. |
| 2009/0088755 | A1 | 4/2009 | Aker et al. |
| 2009/0088758 | A1 | 4/2009 | Bennett |
| 2009/0088759 | A1 | 4/2009 | Aram et al. |
| 2009/0088760 | A1 | 4/2009 | Aram et al. |
| 2009/0088761 | A1 | 4/2009 | Roose et al. |
| 2009/0088763 | A1 | 4/2009 | Aram et al. |
| 2009/0093816 | A1 | 4/2009 | Roose et al. |
| 2009/0099567 | A1 | 4/2009 | Zajac |
| 2009/0110498 | A1 | 4/2009 | Park et al. |
| 2009/0131941 | A1 | 5/2009 | Park et al. |
| 2009/0131942 | A1 | 5/2009 | Aker et al. |
| 2009/0138020 | A1 | 5/2009 | Park et al. |
| 2009/0157083 | A1 | 6/2009 | Park et al. |
| 2009/0222014 | A1 | 9/2009 | Bojarksi et al. |
| 2009/0222016 | A1 | 9/2009 | Park et al. |
| 2009/0222103 | A1 | 9/2009 | Fitz et al. |
| 2009/0226068 | A1 | 9/2009 | Fitz et al. |
| 2009/0228113 | A1 | 9/2009 | Lang et al. |
| 2009/0254093 | A1 | 10/2009 | White et al. |
| 2009/0270868 | A1 | 10/2009 | Park et al. |
| 2009/0276045 | A1 | 11/2009 | Lang |
| 2009/0306676 | A1 | 12/2009 | Lang et al. |
| 2009/0307893 | A1 | 12/2009 | Burdulis, Jr. et al. |
| 2009/0312805 | A1 | 12/2009 | Lang et al. |
| 2010/0023015 | A1 | 1/2010 | Park |
| 2010/0042105 | A1 | 2/2010 | Park et al. |
| 2010/0049195 | A1 | 2/2010 | Park et al. |
| 2010/0054572 | A1 | 3/2010 | Tsougarakis et al. |
| 2010/0082035 | A1 | 4/2010 | Keefer |
| 2010/0087829 | A1 | 4/2010 | Metzger et al. |
| 2010/0152741 | A1 | 6/2010 | Park et al. |
| 2010/0152782 | A1 | 6/2010 | Stone et al. |
| 2010/0160917 | A1 | 6/2010 | Fitz et al. |
| 2010/0168754 | A1 | 7/2010 | Fitz et al. |
| 2010/0174376 | A1 | 7/2010 | Lang et al. |
| 2010/0185202 | A1 | 7/2010 | Lester et al. |
| 2010/0191244 | A1 | 7/2010 | White et al. |
| 2010/0212138 | A1 | 8/2010 | Carroll et al. |
| 2010/0217270 | A1 | 8/2010 | Polinski et al. |
| 2010/0217338 | A1 | 8/2010 | Carroll et al. |
| 2010/0228257 | A1 | 9/2010 | Bonutti |
| 2010/0234849 | A1 | 9/2010 | Bouadi |
| 2010/0256479 | A1 | 10/2010 | Park et al. |
| 2010/0262150 | A1 | 10/2010 | Lian |

(56) References Cited

U.S. PATENT DOCUMENTS

| | | |
|---|---|---|
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0290272 A1 | 11/2012 | Bryan |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0035761 A1 | 2/2013 | Sharkey et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0173926 A1 | 7/2013 | Morese et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0274778 A1 | 10/2013 | Mercier et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |

(56) References Cited

U.S. PATENT DOCUMENTS

| | | |
|---|---|---|
| 2014/0074441 A1 | 3/2014 | Fitz et al. |
| 2014/0086780 A1 | 3/2014 | Miller et al. |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 | 3/2011 |
| DE | 60239674 | 5/2011 |
| DE | 602004032166 | 5/2011 |
| DE | 602005027391 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |

(56) References Cited

FOREIGN PATENT DOCUMENTS

| | | | |
|---|---|---|---|
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Hofmann et al, "Natural-Knee II System", Intermedics Orthopedics, Austin, TX, 1995.

* cited by examiner

COMPUTER ASSISTED SUBCHONDRAL INJECTION

CROSS-REFERENCE TO RELATED APPLICATION

The present application claims priority of provisional U.S. Provisional Patent Application Ser. No. 61/833,652, filed on Jun. 11, 2013, incorporated herein by reference.

FIELD OF THE INVENTION

The present application relates to subchondral injection as performed in computer-assisted surgery.

BACKGROUND OF THE ART

In some patients, some subchondral voids are formed in the bone structure at joints, which voids may weaken the bone. The voids are typically in the trabecular bone structure. In such cases, for some patients, it may not be necessary to use implants, as the injection of a compound in such voids may suffice in solidifying the bone. It would be desirable to use computer assistance to render subchondral injection minimally invasive and ensure the adequate injection of compound or filler material in bone voids.

SUMMARY

Therefore, there is provided a novel method for assisting subchondral injection.

In accordance with the present disclosure, there is provided a method for assisting subchondral injection comprising: creating a model of bone and soft tissue of a patient; modeling at least one void in the bone from the model of bone and soft tissue; identifying an injection site from the model of bone and soft tissue and modeling of the at least one void; and outputting data for guiding at least in the locating of the injection site and drilling of the bone to reach the void.

Further in accordance with the present disclosure, void filling parameters are calculated from the modeling of the at least one void.

Still further in accordance with the present disclosure, calculating void filling parameters comprises calculating a volume of filler material to be injected.

Still further in accordance with the present disclosure, outputting data comprises outputting a model of a patient specific jig, the patient specific jig having at least one component positioned relative to the injection site to guide instrument manipulation at the injection site.

Still further in accordance with the present disclosure, identifying an injection site from the model of bone and soft tissue comprises identifying a percutaneous abutment location, and wherein outputting the model of the patient specific jig comprises outputting the model of the jig with abutments for percutaneous abutment against the leg at the percutaneous abutment location.

Still further in accordance with the present disclosure, outputting the model of the patient specific jig comprises outputting the model with the component being a drill guide for drilling a hole in the bone at the injection site.

Still further in accordance with the present disclosure, outputting the model of the patient specific jig comprises outputting the model with the component being an injection guide for positioning an injection device relative to the injection site.

In accordance with the present disclosure, there is provided a patient-specific jig for subchondral injection, comprising: a structure; abutments on the structure, a position of the abutments in the structure based on a patient-specific bone and soft tissue model, the abutments each having a contour-matching surface fabricated as a function of planned abutment locations of the patient-specific bone and soft tissue model; and at least one guiding component in the structure, a position of the at least one guiding component in the structure based on a planned injection site on the patient-specific bone and soft tissue model, the at least one guiding component adapted to guide a tool for effecting subchondral injection surgery.

Further in accordance with the present disclosure, a patient-specific file comprising a 3-D model of a bone and soft tissue of the patient is provided.

Still further in accordance with the present disclosure, the at least one guiding component is a tube adapted to receive therein at least one of the drill bits and an injection device.

Still further in accordance with the present disclosure, the tube has a height selected as a function of a depth of the drilling tool.

Still further in accordance with the present disclosure, the abutments are percutaneous abutments, the abutments having the contour-matching surface fabricated taking into consideration soft tissue on the bone.

Still further in accordance with the present disclosure, the abutments abut against soft tissue covering at least two bones.

Still further in accordance with the present disclosure, a second structure is connected to a distal location of the planned injection site, an interface between the structure and the second structure.

Still further in accordance with the present disclosure, the interface comprises a telescopic joint.

DETAILED DESCRIPTION

Figure 1:
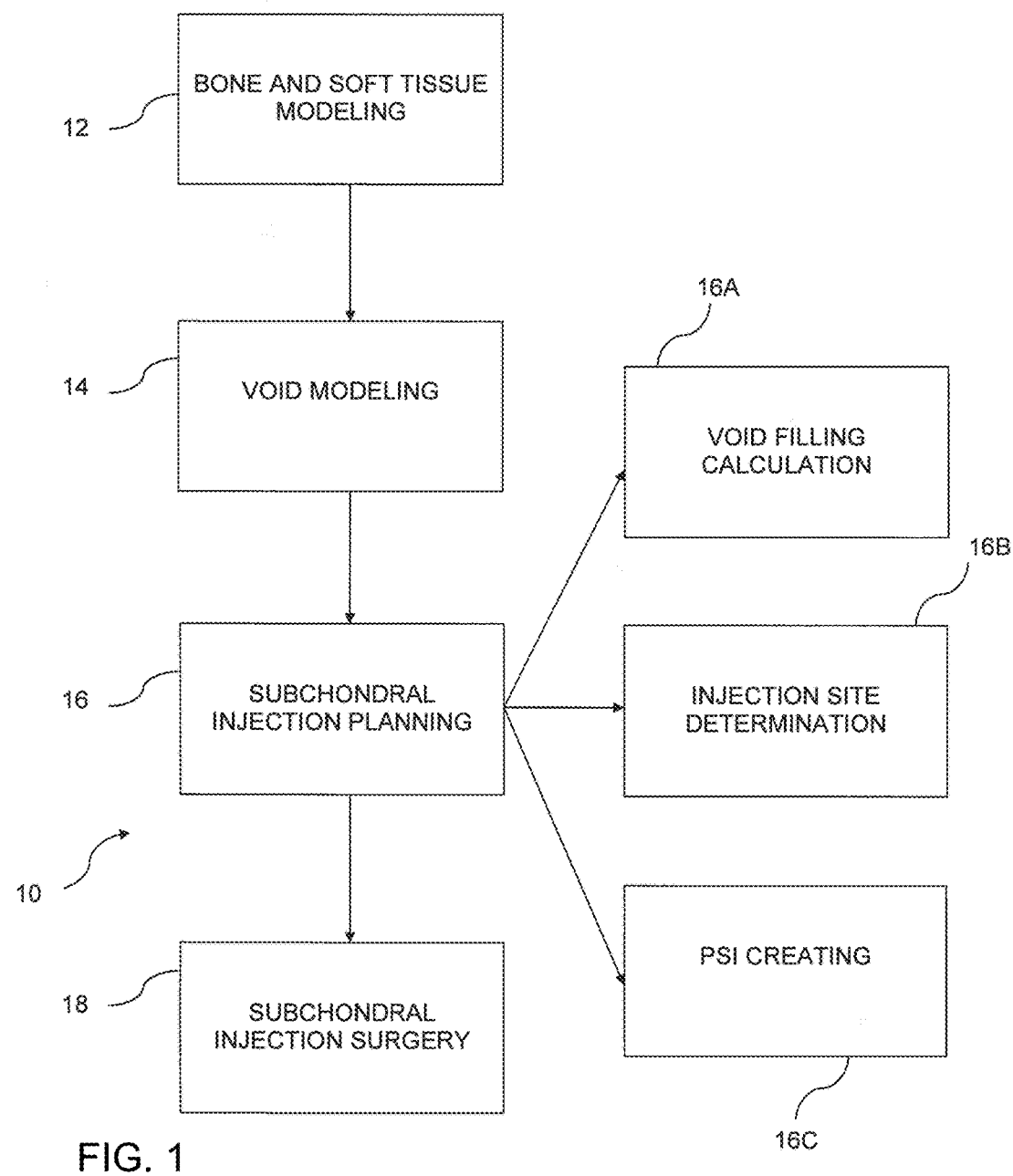
FIG. 1 is a flowchart showing a method for planning and executing subchondral injection surgery, in accordance with the present disclosure.

Referring to FIG. 1, there is illustrated a method for planning and executing subchondral injection surgery at 10. The method 10 may be performed on any appropriate bone (e.g., spinal applications), but is typically used for subchondral injection in either one of the tibia and femur at the knee joint. The method 10 is used to inject a compound or filler material through cortical bone structure into voids of trabecular bone structure.

According to step 12, the bone and soft tissue are modeled. The modeling is typically a three-dimensional (3D) reconstruction based on the segmentation of magnetic resonance imagery (MRI). The segmented structures may potentially include: the bone, the bone void, cartilage, the skin and various types of soft tissue. Other appropriate types of imagery techniques may be used to enable the modeling performed in step 12, such as radiography. MRI reconstruction is however well suited for the method 10 as it allows to see the voids in the bone.

According to step 14, the voids are modeled or identified using the bone and soft tissue models obtained in step 12. By way of the void modeling of step 12, the size (i.e., volume) and location of the voids are determined relative to the bone and soft tissue model of step 12. The void modeling 14 may be performed with the assistance of an operator looking at the images obtained in step 12 and may include various manipulations on the images (segmentation) to delimit the void and hence enable the calculation of the void size and location.

According to step 16, subchondral injection is planned. The planning may include various steps. For instance, according to substep 16A, a void filling calculation is performed to determine the volume of compound that is necessary for each void to be filled. The calculation may also include parameters and simulations such as the flow rate of compound to be administered by the instrument (e.g., syringe), the bone density in the void, and a flow simulation with pressure profile to avoid any overflow of compound outside of the bone.

According to substep 16B, the planning may include injection site determination. Injection site determination comprises identifying a location on the bone that may be drilled or pierced for injection of the compound therethrough. Injection site determination as in 16B may include factors as surrounding soft tissue from the models of step 12, and bone structure (e.g., thickness of cartilage and cortical bone structure) again using the bone models of step 12. Substep 16B may include calculating a drilling depth required to reach the void and determining a drilling diameter.

The subchondral injection planning 16 may also include PSI (Patient Specific Instrumentation) creating as in substep 16C. In the event that the method 10 is used with patient specific instrumentation, PSI creating as in substep 16C entails identifying locations on the leg upon which a support jig may be abutted relative to the injection site identified in substep 16B. In an embodiment, the jigs are made for percutaneous abutment. The PSI creating as in substep 16C takes into consideration the bone and soft tissue modeling of the step 12 to identify adequate leg locations for abutment. It is desired that the actual injection site be as close as possible to the planned injection site identified in substep 16B, whereby abutment locations on the leg are typically where soft tissue is relatively thin and thus allows minimized movements of a support jig thereon relative to the bone. For the knee joint, examples of locations that could be used as abutments are the malleoli, such as the posterior aspect of the malleoli, the talus, the epicondyles (e.g., posterior aspect of epicondyles), the tibial tuberosity, the anterior aspect of tibial shaft, the proximal area of the fibula, and the patella (if it is in the same position as where it was on bone models of step 12). These are only provided as examples, but may be used for knee joint.

Figure 2:
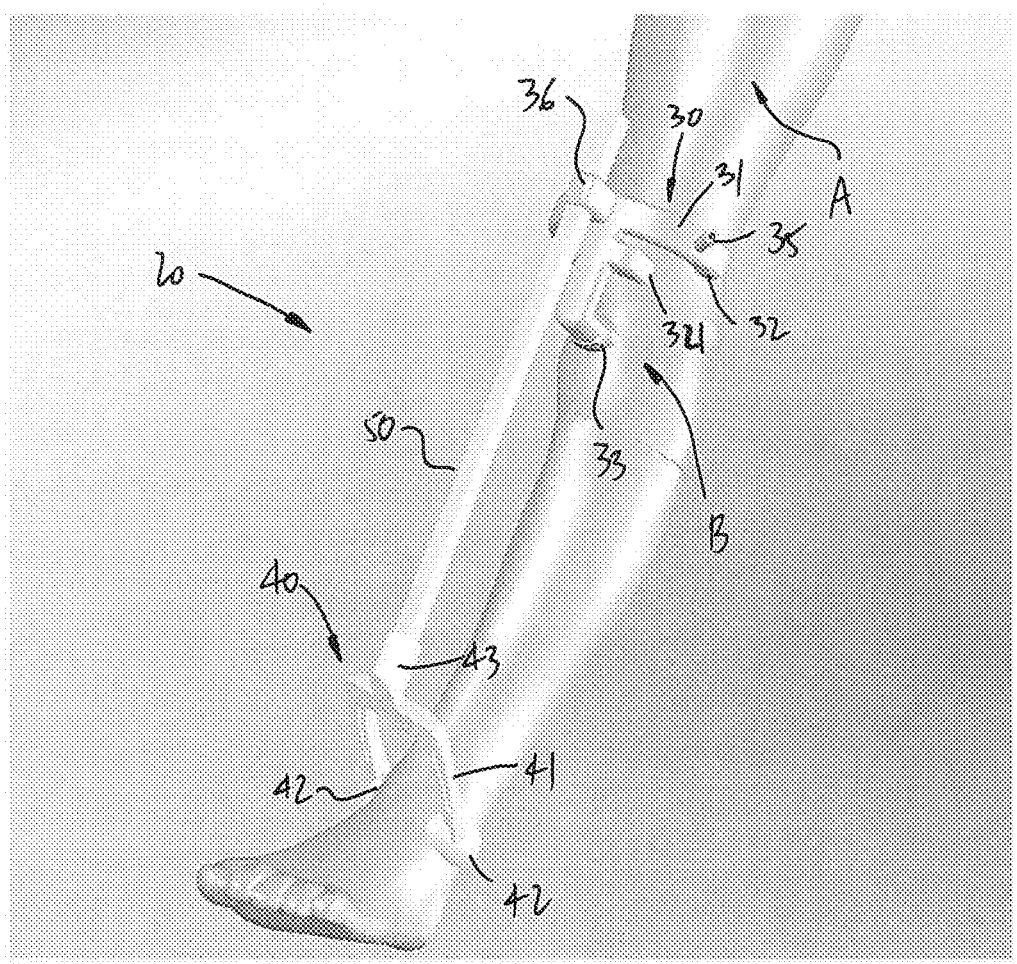
FIG. 2 is a perspective view of a PSI jig in accordance with the present disclosure as positioned on a leg.
Figure 3:
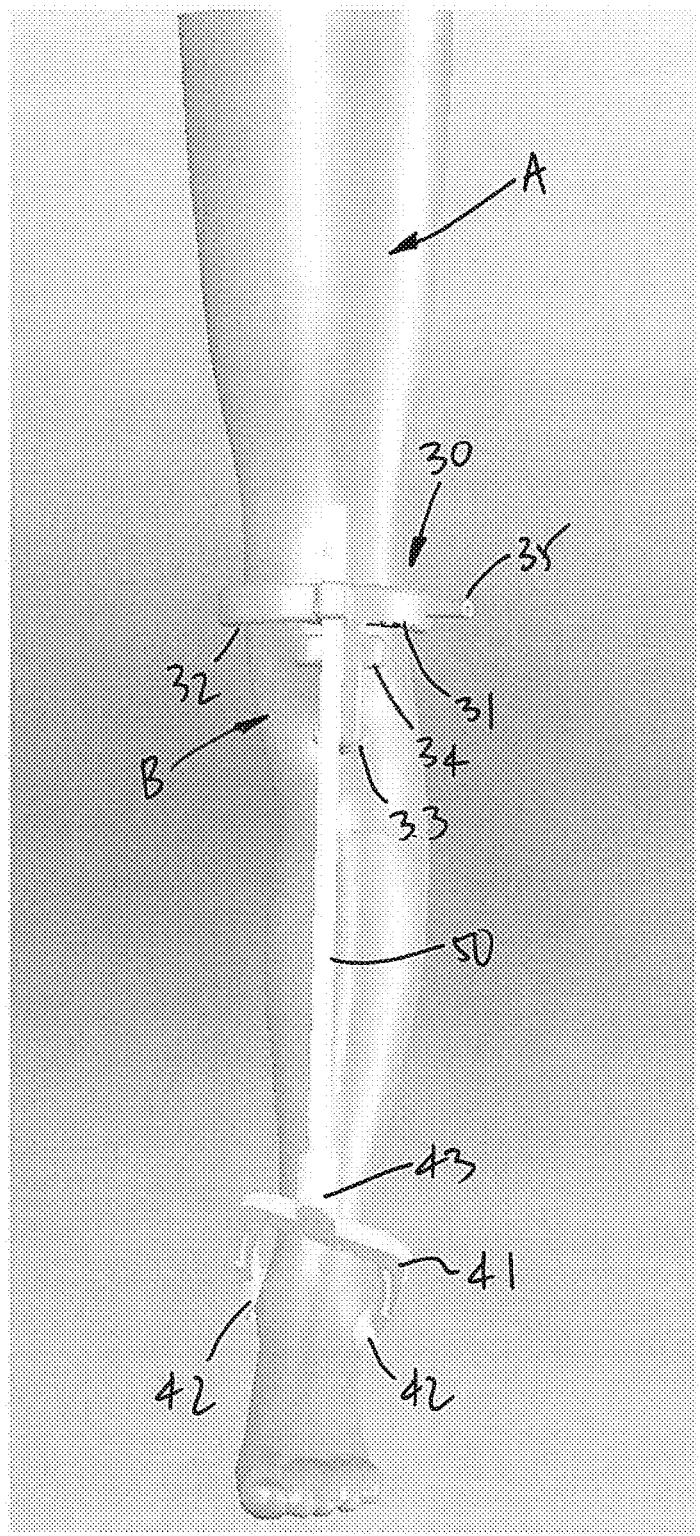
FIG. 3 is an elevation view of the PSI jig of FIG. 2.
Figure 4:
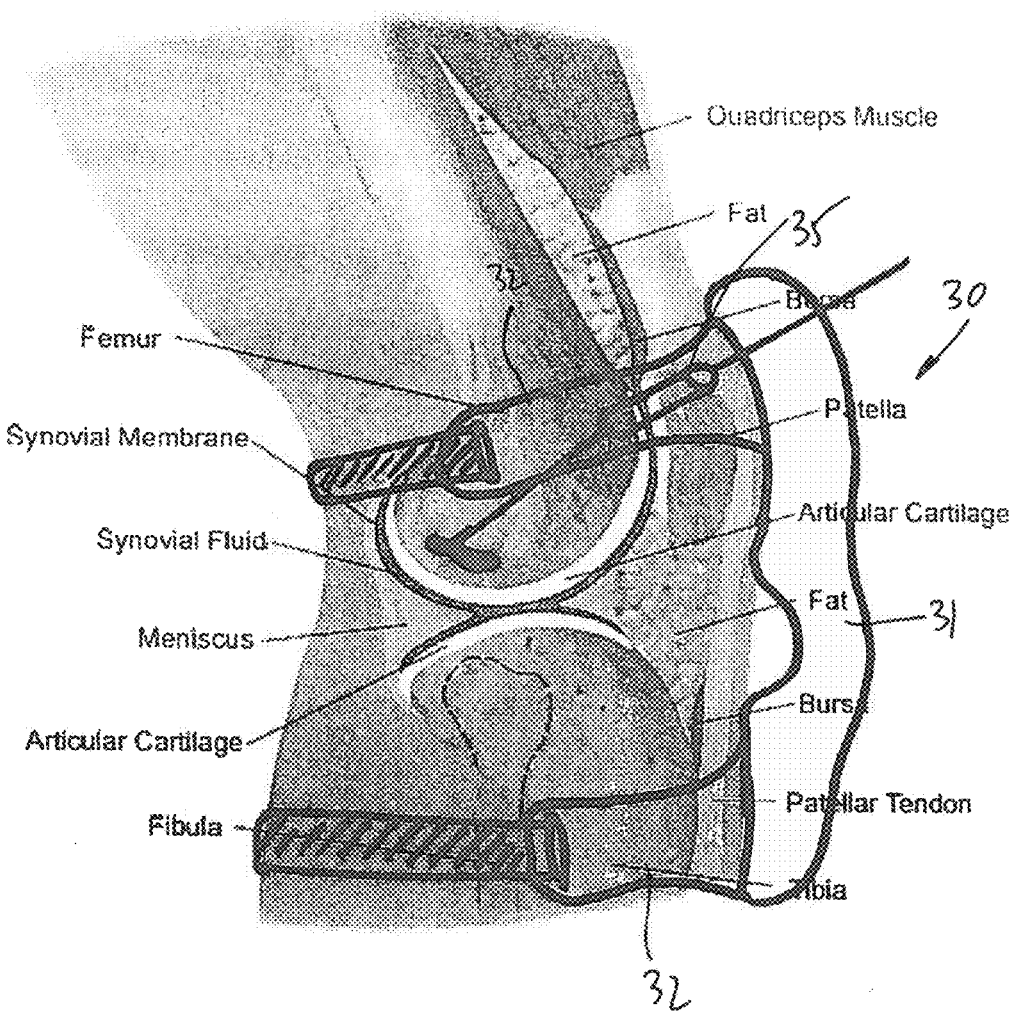
FIG. 4 is a schematic view of a PSI jig in accordance with the present disclosure.

There is shown in FIGS. 2-4 some jigs fabricated using patient-specific technology, to abut percutaneously against selected locations of the leg at the knee joint for subchondral injection, and will be described hereinafter. It is also considered to abut the jig directly against the bone, although it may be desired to opt for percutaneous abutment to render the surgery minimally invasive.

With all information obtained from the planning of step 16, the operator may proceed with subchondral injection surgery as in step 18. Depending on whether patient specific instrumentation or other type of guidance (such as optical navigation) is used, various steps may be performed during subchondral injection surgery as supported by a computer.

The PSI jig is manufactured specifically for the patient as shown in FIGS. 2 and 3, so as to support various instruments that will help the operator in locating the injection site as planned, in drilling or piercing the cartilage and cortical bone structure at the location site. For instance, the PSI jig may have a depth indicator for the drilling depth to be monitored as planned. The PSI jig may or may not be used to guide the manipulations of the injection tools (e.g., syringe). The PSI jig may be a guide channel located opposite the injection site, as planned due to PSI technology, whereby the jig abuts against the leg at desired locations.

Alternatively, optical navigation may be used. In such a case, a registration pointer may be used to reference the bones relative to the 3D models of step 12, for subsequent optical navigating of the tools relative to the bone. The registration pointer is typically used to identify landmark points on the bone (e.g., percutaneous registration may suffice), with the points gathered used to reference the actual bone to the models of step 12. This results in navigation being possible for tools such as a drill for the piercing of a hole at the planned injection site and an injection syringe for the injection of the compound therethrough.

It is also considered to use local fluoroscopy imaging prior to or during the drilling to ensure that the location sites are correctly placed and are opposite the voids in the bone, or to verify that the void filling procedure adequately filled the voids.

Referring to FIGS. 2 and 3, a PSI jig in accordance with an embodiment of the present disclosure is generally shown at 20. The PSI jig 20 is of the type used to drill a hole in a knee femur A at a knee B for subsequent subchondral injection surgery as in item 18 of FIG. 1. The PSI jig 20 may be the result of various steps of the method 10 of FIG. 1. The PSI jig 20 has a knee jig portion 30, an ankle jig portion 40, and a bar 50.

The knee jig portion 30 is adapted to position itself percutaneously on the femur side of the knee B.

The ankle jig portion 40 positions itself percutaneously on the ankle and, more particularly, against the malleoli, and provides additional stability to the PSI jig 20.

The bar 50 interfaces the knee jig portion 30 to the ankle jig portion 40.

FIG. 4 shows embodiments in which a knee jig portion 30 is used without the ankle jig portion 40 and the bar 50, with straps anchoring the knee jig portion 30 to the knee B. However, the embodiment of FIG. 2 is well suited to provide a stable connection of the PSI jig 20 to the leg, with the desired alignment of the PSI jig 20 relative to the injection site.

The knee jig portion 30 has a body or structure 31. The body 31 may be, as in FIG. 2, an arch that has abutment pads 32 to abut percutaneously against landmarks of the femur A. The abutment pads 32 are patient-specific, in that their contact surfaces are machined in contour-matching geometry to be a replica of the site against which they will abut. Likewise, an abutment pad 33, projecting downwardly from the body 31, may be used as an abutment against the kneecap, again with a contour-matching surface made as per the method 10. Additional support may be provided by abutment pad 34.

Guiding tube 35 is one of the possible configurations used to provide guidance to tools. The guiding tube 35 may adequately be positioned to orient a drill bit and an injection device relative to the planned injection site of 16 (FIG. 1). It is also observed that the guide tube 35 may have a given height taking into consideration a drill stop, so as to control the depth of drilling of a drill bit entering the guide tube 35.

Bar interface 36 projects upwardly from the body 31, and will host the bar 50 in telescopic relation.

The ankle jig portion 40 also has a body 41 shaped as an arch at the ends of which are abutment pads 42. While the abutment pads 42 may be patient-specific, it is also considered to have generic abutment pads, with a telescopic relation between the bar 50 and the bar interface 36, simply to provide leveraging support for the knee jig portion 30, which knee jig portion 30 is the component of the PSI jig 20 that must be positioned with highest precision. The ankle jig portion 40 has a bar interface 43 to receive an end of the bar 50. As shown, the bar interface 36 of the knee jig portion 30 forms a prismatic joint with the bar 50, so as to enable the telescopic relation between the knee jig portion 30 and the ankle jig portion 40.

The PSI jig 20 is given as an exemplary embodiment of a jig that may be used to help in performing the subchondral injection surgery according to planning.

The invention claimed is:

1. A method for assisting subchondral injection comprising:
    obtaining, using a processor of a computer, a model of bone and soft tissue of a patient, the model including cortical bone structure and trabecular bone structure for a bone;
    identifying and delimiting, using the processor of the computer, at least one void in the trabecular bone structure formed under cortical bone structure of the bone from the model of bone and soft tissue;
    identifying, using the processor of the computer, an injection site in the cortical bone structure from the model of bone and soft tissue and modeling of the at least one void;
    calculating, using the processor of the computer, a drilling depth to reach the at least one void in the trabecular bone structure;
    calculating and outputting, using the processor of the computer, navigation data for guiding at least a drilling tool relative to the injection site for drilling of the bone at the injection site to the drilling depth to reach the at least one void in the trabecular bone structure;
    tracking, with the processor of the computer, a registration tool identifying landmark points on the bone to reference the landmark points to the model of the bone and soft tissue; and
    navigating, with the processor of the computer, the drilling tool toward the injection site using the reference between the landmark points to the model of the bone and soft tissue and drilling the cortical bone structure to the drilling depth to reach the at least one void in the trabecular bone structure.

2. The method according to claim 1, further comprising calculating void filling parameters from the modeling of the at least one void.

3. The method according to claim 2, wherein calculating void filling parameters comprises calculating a volume of filler material to be injected.

4. The method according to claim 1, wherein obtaining the model of bone and soft tissue includes creating the model of bone and soft tissue using three-dimensional reconstruction from imagery.

5. The method according to claim 4, wherein creating the model of bone and soft tissue includes using one of magnetic resonance imagery and radiography.

6. The method according to claim 1, further obtaining the model of bone and soft tissue includes obtaining a three-dimensional model, and wherein identifying and delimiting the at least one void includes delimiting the at least one void in three dimensions.

7. The method according to claim 1, wherein outputting navigation data includes outputting a navigation of the drilling tool relative to the bone.

8. The method according to claim 7, wherein outputting a navigation of the drilling tool relative to the bone includes outputting optical navigation data.

9. The method according to claim 1, wherein outputting navigation data includes outputting in the navigation data a drilling stop based on said drilling depth.

10. The method according to claim 1, wherein identifying and delimiting at least one void includes identifying and delimiting at least one void present in the trabecular bone structure prior to surgery.

11. A method for assisting subchondral injection comprising:
    obtaining, using a processor of a computer, a model of bone and soft tissue of a patient, the model including cortical bone structure and trabecular bone structure for a bone;
    identifying and delimiting, using the processor of the computer, at least one void in the trabecular bone structure formed under cortical bone structure of the bone from the model of bone and soft tissue;
    identifying, using the processor of the computer, an injection site in the cortical bone structure from the model of bone and soft tissue and modeling of the at least one void;
    identifying a percutaneous abutment location in relation to the injection site;
    calculating and outputting, using the processor of the computer, a model of a patient specific jig, the patient specific jig having at least one component positioned relative to the injection site to guide a drilling tool at the injection site, and a contour-matching geometry matching a geometry of the percutaneous abutment location, the contour-matching geometry for percutaneous abutment of the patient specific j against a leg of the patient at the percutaneous abutment location; and
    fabricating the patient specific jig with the at least one component to wide the drilling tool and the contour-matching geometry using the model of the patient specific jig.

12. The method according to claim 11, wherein outputting the model of the patient specific jig comprises outputting the model with the component being a drill guide for drilling a hole in the bone at the injection site.

13. The method according to claim 11, wherein outputting the model of the patient specific jig comprises outputting the model with the component being an injection guide for positioning an injection device relative to the injection site.

14. The method according to claim 11, wherein fabricating the patient specific jig with the contour-matching geometry comprises machining the patient specific jig with the contour-matching geometry.

15. The method according to claim 11, wherein obtaining the model of bone and soft tissue includes creating the model of bone and soft tissue using three-dimensional reconstruction from imagery includes creating the model of bone and soft tissue using one of magnetic resonance imagery and radiography.

16. The method according to claim 11, wherein identifying and delimiting at least one void includes identifying and delimiting at least one void present in the trabecular bone structure prior to surgery and formed under cortical bone structure.

* * * * *